(12) United States Patent
Li et al.

(10) Patent No.: US 11,795,174 B2
(45) Date of Patent: Oct. 24, 2023

(54) ANTI-PAIN COMPOUND AND PREPARATION METHOD THEREOF

(71) Applicant: LUNAN PHARMACEUTICAL GROUP CORPORATION, Shandong (CN)

(72) Inventors: Runtao Li, Beijing (CN); Jia Ye, Beijing (CN); Xin Wang, Beijing (CN); Zemei Ge, Beijing (CN); Yingying Liang, Beijing (CN); Xiaolei Du, Beijing (CN); Ding Wang, Beijing (CN); Guimin Zhang, Linyi (CN); Jingchun Yao, Linyi (CN); Guifang Zhao, Linyi (CN)

(73) Assignee: LUNAN PHARMACEUTICAL GROUP CORPORATION, Linyi (CN)

( * ) Notice: Subject to any disclaimer, the term of this patent is extended or adjusted under 35 U.S.C. 154(b) by 0 days.

(21) Appl. No.: 16/770,533

(22) PCT Filed: Dec. 7, 2018

(86) PCT No.: PCT/CN2018/119785
§ 371 (c)(1),
(2) Date: Jun. 5, 2020

(87) PCT Pub. No.: WO2019/110006
PCT Pub. Date: Jun. 13, 2019

(65) Prior Publication Data
US 2020/0369674 A1   Nov. 26, 2020

(30) Foreign Application Priority Data

Dec. 7, 2017   (CN) .......................... 201711334106.5

(51) Int. Cl.
*C07D 487/10* (2006.01)
*A61P 29/00* (2006.01)

(52) U.S. Cl.
CPC ............ *C07D 487/10* (2013.01); *A61P 29/00* (2018.01)

(58) Field of Classification Search
CPC ................................ C07D 487/10; A61P 29/00
See application file for complete search history.

(56) References Cited

U.S. PATENT DOCUMENTS

| | | | |
|---|---|---|---|
| 9,133,195 B2 * | 9/2015 | Li | ......................... A61P 43/00 |
| 2011/0021781 A1 | 1/2011 | Gupta et al. | |
| 2013/0035329 A1 | 2/2013 | Saunders et al. | |
| 2017/0340623 A1 | 11/2017 | Charmot et al. | |
| 2018/0298002 A1 | 10/2018 | Horenstein et al. | |

FOREIGN PATENT DOCUMENTS

| | | | |
|---|---|---|---|
| CN | 101089000 A | | 12/2007 |
| CN | 102786497 A | * | 11/2012 |
| EP | 2036909 A1 | | 3/2009 |
| GB | 2435828 A | | 9/2007 |
| JP | 2009539889 A | | 11/2009 |
| JP | 2014114300 A | | 6/2014 |
| JP | 2015193633 A | | 11/2015 |
| RU | 2010142500 A | | 4/2012 |
| WO | 2017/066558 A1 | | 4/2017 |

OTHER PUBLICATIONS

Registry No. 1239959-02-4, File Registry on STN, Sep. 3, 2010.*
International Search Report from International Application No. PCT/CN2018/119785, dated Mar. 12, 2019.
Written Opinion from International Application No. PCT/CN2018/119785, dated Mar. 12, 2019.
First Office Action from corresponding Chinese Patent Application No. 201711334106.5, dated Dec. 24, 2019.
Mokrosz et al., "Structure-activity relationship studies of central nervous system (CNS) agents. 5. Effect of the hydrocarbon chain on the affinity of 4-substituted 1-(3-chlorophenyl)piperazines for 5-HT1A receptor sites", Journal of Medicinal Chemistry, vol. 35, Dec. 31, 1992 (Dec. 31, 1992), pp. 2369-2374.
Extended European Search Report for European Patent Application No. 18886979.6 dated Jul. 29, 2021, 8 pages.

(Continued)

*Primary Examiner* — Rebecca L Anderson
(74) *Attorney, Agent, or Firm* — Merchant & Gould P.C.

(57) ABSTRACT

Disclosed are a compound represented by the general Formula (I), or a stereisomer, tautomer, derivative, prodrug or pharmaceutically acceptable salt thereof, and a method for preparing the compound and use of the compound in manufacture of a medicament for treating a neuropathic pain and/or neuropathic pain syndrome or a medicament for combating an inflammation:

(I)

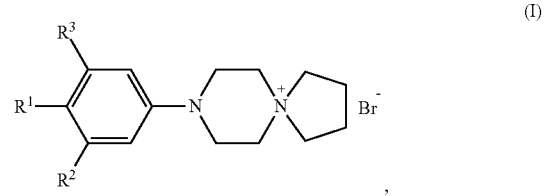

wherein $R^1$ is selected from hydrogen, halogen, alkyl, cyano and haloalkyl, $R^2$ and $R^3$ are independently selected from hydrogen, halogen, alkyl, haloalkyl and nitro, and $R^1$, $R^2$ and $R^3$ are not hydrogen at the same time; furthermore, when either $R^2$ or $R^3$ is nitro or halogen, the other two of $R^1$, $R^2$ and $R^3$ are not hydrogen at the same time. The compound has good effects in treating a neuropathic pain and/or neuropathic pain syndrome and good effects in combating an inflammation, and has not side effects such as addiction.

15 Claims, No Drawings

(56) References Cited

OTHER PUBLICATIONS

Sun Qi, et al., "Unique spirocyclopiperazinium salt III: Further investigation of monospirocyclopiperazinium (MSPZ) salts as potential analgesics", Bioorganic & Medicinal Chemistry Letters, 2007, pp. 6245-6249, vol. 17, No. 22.
Chinese Office Action for CN Application No. 201880077143.9 dated Oct. 13, 2021 (16 pages, with English translation).
Indian Examination Report for IN Application No. 202037028597 dated Dec. 15, 2021 (6 pages, with English translation).
Japanese Office Action for JP Application No. 2020-530682 dated Jan. 26, 2022 (7 pages, with English translation).
Registry No. 1240015-57-9, Filed Registry (STN) [online] Sep. 5, 2010.
Belikov, "Relationship Between the Chemical Structure, Properties of Substances and their Effect on the Body," M: MEDpress-inform, 2007, p. 27-29 (English Abstract).

* cited by examiner

ANTI-PAIN COMPOUND AND PREPARATION METHOD THEREOF

This application is a National Stage Application of International Application No. PCT/CN2018/119785, filed 7 Dec. 2018, which claims benefit of Serial No. 201711334106.5, filed 7 Dec. 2017 in China. To the extent appropriate, a claim of priority is made to each of the above disclosed applications.

TECHNICAL FIELD

The invention relates to a new compound for treating a neuropathic pain and/or neuropathic pain syndrome, and its preparation method and use.

BACKGROUND ART

Pain is a common disease, and there are three categories of pains: physiological pain, inflammatory pain, and neuropathic pain (NPP).

Neuropathic pain is a relatively common type of disease in clinical practice. In 2008, the International Association for the Study of Pain (IASP) defined it as "a pain caused by damage or disease of somatosensory system". Neuropathic pain is caused by, for example, injury or dysfunction of the peripheral or central nervous system, and is a stubborn chronic pain without effective treatment means in clinic. Diseases of neuropathic pain include, for example, diseases showing symptoms of hyperalgesia or allodynia, such as postherpetic neuralgia, trigeminal neuralgia, diabetic neuralgia, and postoperative or post-traumatic pain. As a worldwide problem, neuropathic pain affects millions of patients worldwide, and seriously affects the life quality of patients.

Although both belong to chronic pain, there is an essential difference between neuropathic pain and inflammatory pain. The methods for treatment of neuropathic pain in the prior art include the use of traditional analgesics such as non-steroidal anti-inflammatory drugs and opioids, as well as other drugs including anticonvulsants and tricyclic antidepressants (Max, M B Ann. Neurol, 35 (Suppl): S50-S53 (1994); Raja, S N et al., Neurology, 59: 1015 (2002); Galer, B S et al., Pain, 80: 533 (1999)). However, these drugs cannot completely relieve pain or have undesirable side effects, such as drug resistance and addiction risk.

Spirocyclopiperazinium salt compounds are a class of compounds obtained by Li Runtao's research group of Peking University based on the structural modification of 1,1-dimethyl-4-phenylpiperazinium iodide (DMPP). It has been reported that spirocyclopiperazinium salt compounds have analgesic activity, and such compounds are not addictive (see Yue, CQ, Ye, J., Li, CL, Li, RT, Sun, Q., 2007. Antinociceptive effects of the novel spirocyclopiperazinium salt compound LXM-10 in mice. Pharmacol Biochem Behav 86, 643-650). Their analgesic mechanism may be related to agonistic cholinergic receptors (see: Zhao, X., Ye, J., Sun, Q., Xiong, Y., Li, R., Jiang, Y., 2011. Antinociceptive effect of spirocyclopiperazinium salt compound LXM-15 via activating peripheral alpha7 nAChR and M4 mAChR in mice. Neuropharmacology 60, 446-452).

However, regarding the analgesic effects of these spirocyclopiperazinium salt compounds, the reports in the prior art merely disclose that these spirocyclopiperazinium salt compounds (especially the compound LXM-10) are effective in inhibiting physiological pains and inflammatory pains (see, e.g., WO2007/147346), but do not describe whether these compounds are effective in treating a neuropathic pain.

Therefore, there is a need to develop a drug that is more effective in treating a neuropathic pain.

Contents of the Invention

In one aspect, the object of the present invention is to provide a new compound, or a stereoisomer, tautomer, derivative, prodrug or pharmaceutically acceptable salt thereof, for treating a neuropathic pain and/or a neuropathic pain syndrome.

In another aspect, the object of the present invention is to provide a method for preparing the above compound.

The present invention provides a compound represented by the following Formula (I), or a stereoisomer, tautomer, derivative, prodrug, or pharmaceutically acceptable salt thereof:

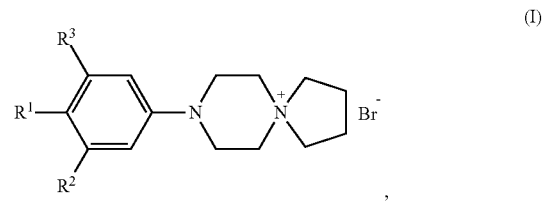

(I)

wherein $R^1$ is selected from the group consisting of hydrogen, halogen, alkyl, cyano and haloalkyl, $R^2$ and $R^3$ are independently selected from the group consisting of hydrogen, halogen, alkyl, haloalkyl and nitro, and $R^1$, $R^2$ and $R^3$ are not hydrogen at the same time;

and, when one of $R^2$ and $R^3$ is nitro or halogen, the remaining two of $R^1$, $R^2$, and $R^3$ are not hydrogen at the same time.

The term "halogen" as used in the present invention refers to a fluorine, chlorine, bromine or iodine atom, preferably a fluorine, chlorine or bromine atom.

As used herein, the term "halo" refers to fluoro, chloro, bromo, or iodo.

The term "alkyl" used in the present invention is a linear or branched alkyl group having 1 to 6 carbon atoms, more preferably a linear or branched alkyl group having 1 to 3 carbon atoms, and particularly preferably methyl, ethyl or propyl.

The term "haloalkyl" as used in the present invention refers to an alkyl group as defined above that is substituted with one or more, preferably one to five halogen atoms, wherein the halogen atoms are those defined in this application. Haloalkyl includes monohaloalkyl, dihaloalkyl, trihaloalkyl, perhaloalkyl, etc., such as chloromethyl, dichloromethyl, difluoromethyl, trifluoromethyl, 2,2,2-trifluoroethyl, perfluoroethyl, 2,2,2-trifluoro-1,1-dichloroethyl, etc. Among them, the haloalkyl may preferably be trihaloalkyl, and more preferably trifluoromethyl.

As used herein, the term "nitro" refers to —$NO_2$ group.

The term "cyano" as used in the present invention refers to —CN group.

In an embodiment of Formula (I) of the present invention, $R^2$ and $R^3$ are independently selected from the group consisting of alkyl, haloalkyl, and nitro, and $R^1$ is hydrogen.

In an embodiment of Formula (I) of the present invention, $R^2$ and $R^3$ are each independently selected from methyl, ethyl, trifluoromethyl or nitro, and $R^1$ is hydrogen.

In an embodiment of the present invention, the compound of the present invention is represented by the following Formula (II):

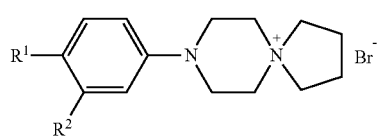

wherein $R^1$ is selected from the group consisting of hydrogen, halogen, alkyl, cyano and haloalkyl, $R^2$ is selected from the group consisting of hydrogen, halogen, alkyl, haloalkyl and nitro, and $R^1$ and $R^2$ are not hydrogen at the same time.

In an embodiment of Formula (II) of the present invention, $R^1$ is selected from the group consisting of halogen, alkyl, cyano and haloalkyl, and $R^2$ is selected from the group consisting of halogen, alkyl, haloalkyl, and nitro.

In an embodiment of Formula (II) of the present invention, $R^1$ is selected from the group consisting of fluorine, chlorine, bromine, methyl, ethyl, cyano and trifluoromethyl, and $R^2$ is selected from the group consisting of fluorine, chlorine, bromine, methyl, ethyl, trifluoromethyl and nitro.

In an embodiment of Formula (II) of the present invention, $R^1$ and $R^2$ are both halogen.

In an embodiment of the present invention, $R^1$ is hydrogen, halogen or haloalkyl; $R^2$ is hydrogen or nitro.

In an embodiment of Formula (II) of the present invention, $R^1$ is alkyl, cyano, halogen or haloalkyl, and $R^2$ is hydrogen.

In an embodiment of Formula (II) of the present invention, $R^1$ is halogen or haloalkyl, and $R^2$ is hydrogen.

In an embodiment of Formula (II) of the present invention, the alkyl is methyl, ethyl or propyl.

In an embodiment of Formula (II) of the present invention, the haloalkyl is trifluoromethyl.

The preferred compounds of the invention are selected from the group consisting of:

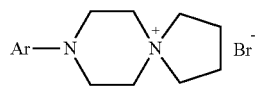

Ar=

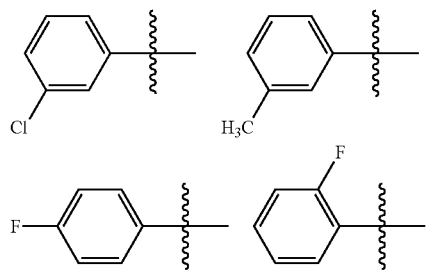

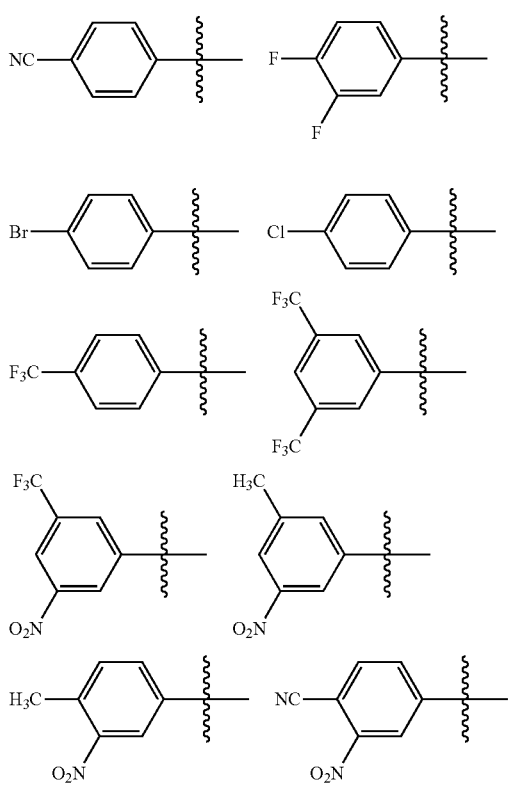

Further preferred compounds of the invention are selected from:

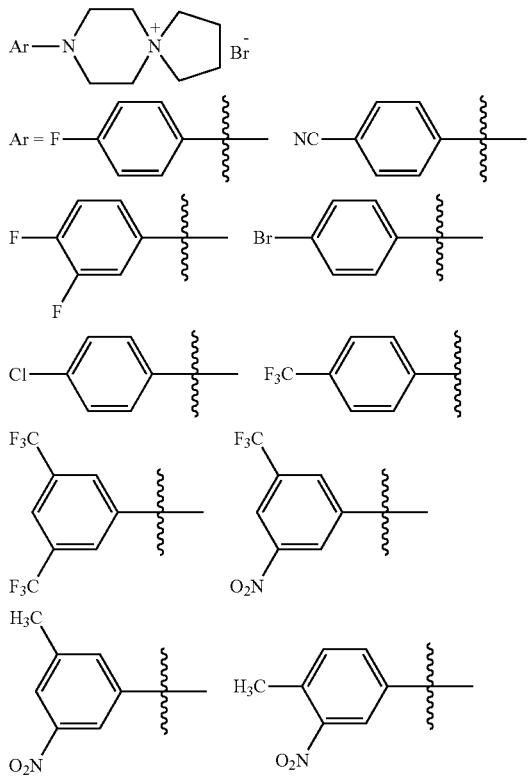

-continued

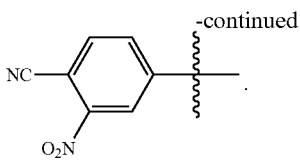

The compounds of the present invention can be prepared according to a conventional method in the art, preferably according to the following reaction scheme:

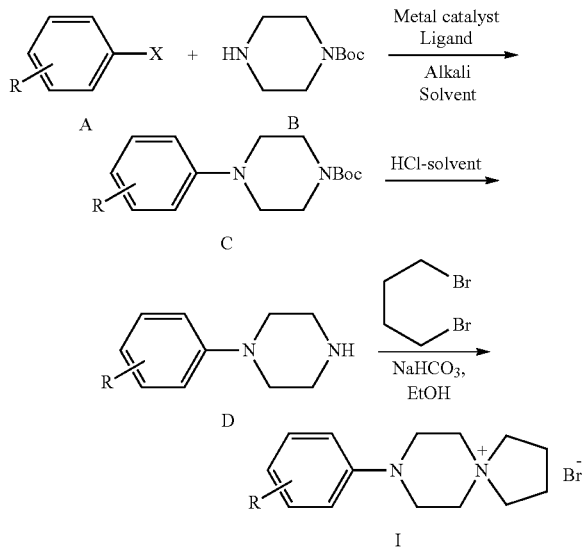

In a preferred embodiment of the present invention, the present invention provides a method for preparing a compound of general Formula (I), the method comprising the following steps:

(1) dissolving a halogenated benzene reagent (A), a metal catalyst, a ligand, and an alkali as raw materials in a solvent, then adding 1-Boc-piperazine (B), and reacting under argon atmosphere at a reaction temperature of 40° C. to 140° C., to obtain an intermediate compound (C);

(2) adding an hydrochloric acid-organic solvent to the intermediate compound (C) and stirring at room temperature to obtain a deprotected intermediate (D); and (3) dissolving the deprotected intermediate (D) into a solvent, and reacting with 1,4-dibromobutane in the presence of NaHCO$_3$ to obtain the compound of the general Formula (I) of the present invention.

In the above method, the halogenated benzene reagent may be selected from the group consisting of trifluoromethyl-substituted bromobenzene, trifluoromethyl-substituted iodobenzene; difluoromethyl-substituted bromobenzene, difluoromethyl-substituted iodobenzene; bromoiodobenzene; nitro-substituted chlorobenzene, nitro-substituted bromobenzene, nitro-substituted iodobenzene, etc.

In the above method, the metal catalyst may be selected from the group consisting of palladium chloride, copper acetate, cuprous iodide, ferric trichloride and the like; preferably cuprous iodide.

In the above method, the ligand may be selected from the group consisting of different a-amino acids, o-hydroxybenzamide, binaphthol, and the like. Among them, the ligand is preferably binaphthol.

In the above method, the alkali may be selected from the group consisting of organic alkalies and inorganic alkalies, such as pyridine, triethylamine, potassium hydroxide, sodium hydroxide, potassium carbonate, sodium carbonate, potassium bicarbonate, sodium bicarbonate, cesium carbonate, potassium phosphate, sodium phosphate, etc. Among them, the alkali is preferably potassium phosphate.

In step (1) of the above method, the solvent as used is an alcohol, ketone, nitrile, chlorinated hydrocarbon solvent, benzene-type solvent, DMSO or DMF, wherein the alcohol solvent is, for example, methanol, ethanol, isopropanol, ethylene glycol, etc.; the ketone solvent is, for example, acetone, methyl ethyl ketone, etc.; the nitrile solvent is, for example, acetonitrile, etc.; the chlorinated hydrocarbon solvent is, for example, dichloromethane, chloroform, etc.; the benzene-type solvent is, for example, benzene, toluene, xylene, etc. The preferred solvent is methanol, ethanol, isopropanol, acetonitrile, acetone, toluene, benzene, DMSO, DMF, chloroform or dichloromethane, and the more preferred solvent is DMF.

In step (1) of the above method, the preferred reaction temperature is 100° C.

In step (1) of the above method, the reaction time may be 6 h to 48 h, preferably 12 h to 32 h, and more preferably 24 h.

In step (2) of the above method, the organic solvent is an alcohol or ester solvent, wherein the alcohol solvent is, for example, methanol, ethanol, isopropanol, ethylene glycol, etc.; wherein, the ester solvent is, for example, ethyl formate, ethyl acetate, methyl acetate, isopropyl acetate, etc. The preferred organic solvent is ethyl acetate.

In the present invention, the room temperature may be 0° C. to 40° C., preferably 10° C. to 30° C., more preferably 15° C. to 25° C.

In step (3) of the above method, the solvent as used is an alcohol, ketone, nitrile, chlorinated hydrocarbon solvent, benzene-type solvent, DMSO or DMF, wherein the alcohol solvent is, for example, methanol, ethanol, isopropanol, ethylene glycol, etc., the ketone solvent is, for example, acetone, methyl ethyl ketone, etc., the nitrile solvent is, for example, acetonitrile, etc., the chlorinated hydrocarbon solvent is, for example, dichloromethane, chloroform, etc., the benzene-type solvent is, for example, benzene, toluene, xylene, etc., the preferred solvent is methanol, ethanol, isopropanol, acetonitrile, acetone, toluene, benzene, DMSO, DMF, chloroform, dichloromethane or ethylene glycol, the more preferred solvent is ethanol.

The target product obtained in the above method can be refined and purified by a conventional method, for example, it can be isolated and purified by recrystallization, and the solvent used for recrystallization can be ethyl acetate-ethanol, acetone-ethanol, ethyl acetate-methanol, acetone-methanol, acetone-water, methanol, ethanol or isopropanol, etc., preferably ethyl acetate-ethanol.

In yet another aspect, the object of the present invention is to provide a pharmaceutical composition comprising the compound of the present invention for treating a neuropathic pain and/or neuropathic pain syndrome, which may further optionally comprise a pharmaceutically acceptable carrier. According to need, the content of the active ingredient in the pharmaceutical composition is in the range of 0.1% to 99%, and the rest is a pharmaceutically acceptable carrier.

The pharmaceutical composition of the present invention can be formulated into various required pharmaceutical dosage forms according to conventional methods in the pharmaceutical field, such as oral preparation, injection, rectal preparation, topical preparation, etc., for example, tablet, pill, dispersed powder, capsule, granule, emulsion, solution, suspension, syrup, solid suppository preparation for vaginal or rectal administration, patch for topical administration, etc. It is preferably formulated as an injection, oral, or transdermal topical dosage form, and particularly preferred as a corresponding sustained-release or controlled-release dosage form.

The pharmaceutical composition of the present invention and various preparations of the composition can be prepared according to conventional methods known in the pharmaceutical field.

In order to prepare a suitable dosage form, a pharmaceutical carrier can be added as needed, including various suitable pharmaceutical adjuvants, such as excipient, filler, diluent, disintegrant, surfactant, wetting agent, preservative, sweetener, pigment, etc.

According to the type and severity of disease and the condition of patient, such as gender, age, body weight, etc., an appropriate dosage form and an administration dose may be selected, and usual administration dose for an adult is 1-200 mg/kg body weight/day, preferably 1-50 mg/kg body weight/day.

In yet another aspect, the object of the present invention is to provide use of a compound of general Formula (I), or a stereoisomer, tautomer, derivative, prodrug or pharmaceutically acceptable salt thereof in the treatment of a neuropathic pain and/or a neuropathic pain syndrome, comprising a step of formulating the above substance into various medicinal dosage forms suitable for administration.

Preferably, the present invention relates to use of compounds DXL-A-16, DXL-A-19, DXL-A-21, DXL-A-22, DXL-A-23, DXL-A-24, or their stereoisomers, tautomers, derivatives, prodrugs or pharmaceutically acceptable salts in the treatment of a neuropathic pain and/or a neuropathic pain syndrome.

In another aspect, the object of the present invention is to provide use of a compound of general Formula (I), or a stereoisomer, tautomer, derivative, prodrug or pharmaceutically acceptable salt thereof in combating an inflammation, comprising formulating the above substance into various medicinal dosage forms suitable for administration.

In another aspect, the object of the present invention is to provide use of a compound of general Formula (I), or a stereoisomer, tautomer, derivative, prodrug or pharmaceutically acceptable salt thereof in the manufacture of a medicament for treating a neuropathic pain and/or a neuropathic pain syndrome.

In another aspect, the object of the present invention is also to provide use of a compound of general Formula (I), or a stereoisomer, tautomer, derivative, prodrug or pharmaceutically acceptable salt in the manufacture of a medicament for combating an inflammation.

Preferably, the present invention relates to use of compounds DXL-A-16, DXL-A-19, DXL-A-21, DXL-A-22, DXL-A-23, and DXL-A-24, or their stereoisomers, tautomers, derivatives, prodrugs or pharmaceutically acceptable salts in the manufacture of a medicament for combating an inflammation.

Another object of the present invention is to provide a method for treating a neuropathic pain and/or a neuropathic pain syndrome, the method comprising administrating a therapeutically effective amount of a compound of general Formula (I), or a stereoisomer, tautomer, prodrug or pharmaceutically acceptable salt thereof to a patient in need of such treatment.

Another object of the present invention is to provide a method for combating an inflammation, the method comprising administrating a therapeutically effective amount of a compound of general Formula (I), or a stereoisomer, tautomer, prodrug or pharmaceutically acceptable salt thereof to a patient in need of such treatment.

According to the present invention, the neuropathic pain is a pain induced or caused by a primary lesion or dysfunction in the central nervous system.

For example, the neuropathic pain syndrome comprises postherpetic neuralgia (which is caused by herpes zoster), root avulsion injury, painful traumatic mononeuropathy, painful polyneuropathy (especially due to diabetes), central pain syndrome (which may be caused by a nervous system damage at almost any level), postoperative pain syndrome (e.g., post-mastectomy syndrome, post-thoracotomy syndrome, phantom pain), and complex regional pain syndrome (reflex sympathetic dystrophy and burning pain).

In some cases, the neuropathic pain has a typical symptom such as dysesthesia (spontaneous or induced burning pain, often with superimposed throbbing pain), but the pain may also be deep and dull pain. Other sensations (such as hyperesthesia, hyperalgesia, allodynia (pain due to harmless stimulation), and hyperalgesia (especially unpleasant, exaggerated pain responses)) may also occur.

According to the present invention, the neuropathic pain can be divided into "peripheral" (originating from the peripheral nervous system) and "central" (originating from the brain or spinal cord).

Central neuropathic pain is a pain with a cause selected from the following: brain lesions mainly in the thalamus; infarction, such as thalamus infarction or brain stem infarction; brain tumor or abscesses that compresses the thalamus or brain stem; multiple sclerosis; split brain operation, such as thalamus incision in the case of dyskinesia; spinal cord lesions; spinal cord injury; spinal cord operation, such as anterior lateral spinal cord amputation; bloody lesions; anterior spinal artery syndrome; lateral medullary syndrome; and syringomyelia.

According to the present invention, the neuropathic pain is a central neuropathic pain syndrome. For example, the central neuropathic pain syndrome is caused by a spinal cord injury and/or a spinal cord contusion.

In some cases, the neuropathic pain is a head pain syndrome caused by a central pain mechanism, such as migraine or migraine pain.

In some cases, the neuropathic pain is a peripheral neuropathic pain. For example, the peripheral neuropathic pain is caused by a chronic compression injury or a sciatic nerve ligation.

According to the present invention, the main peripheral neuropathic pains include neuropathic pains selected from the following types and/or neuropathic pains with causes selected from the followings: systemic diseases, such as diabetic neuropathy; drug-induced diseases, such as neuropathy caused by chemotherapy; post-traumatic syndrome and entrapment syndrome; nerve root and ganglion diseases; neuropathy after HIV infection; neuralgia after herpes infection; nerve root tear; cranial neuropathy; cranial neuralgia, such as trigeminal neuralgia; neuropathic cancer pain; phantom pain; compression of peripheral nerve, nerve plexus and nerve root; paraneoplastic peripheral neuropathy and ganglion diseases; complications of cancer treatment, such as chemotherapy, radiation and surgery; complex regional pain syndrome; type I lesions (formerly known as sympathetic reflex dystrophy); and type II lesions (roughly equivalent to burning pain).

The compound of general Formula (I) of the present invention, or a stereoisomer, tautomer, prodrug or pharmaceutically acceptable salt thereof has a good effect in the treatment of a neuropathic pain and/or neuropathic pain syndrome and in combating an inflammation, and has no addiction side effect.

SPECIFIC MODELS FOR CARRYING OUT THE INVENTION

Next, the present invention will be described in detail through the following examples.

Those skilled in the art will understand that the following examples are only for illustrating the present invention and should not be considered as limiting the scope of the present invention. If specific technology or conditions were not given in the examples, the technology or conditions described in the literature in the art or the product instruction should be followed. If the manufacturers of reagents or instruments as used were not given, they were all conventional products that could be obtained through purchase.

Reagents and solvents were commercially available in chemically pure or analytically pure. Unless otherwise stated, they were used without further treatment. Petroleum ether was a fraction of 60-90° C., anhydrous dioxane was dried by activated molecular sieve, and anhydrous THF was treated by sodium. The raw materials and reagents were made in China, or by Arcos Company, Saen Company, Innochem Company, etc.

Column chromatography: silica gel 200-300 mesh from Qingdao Ocean Chemical Factory, color developing agent, iodine, or UV light detection.

Nuclear magnetic resonance instrument: BrukerAVANCE III 400; high-resolution mass spectrometry: Waters Xevo G2 Q-TOF liquid chromatography-mass spectrometer.

General Method I of Synthesis (Taking Compound DXL-A-10 as an example)

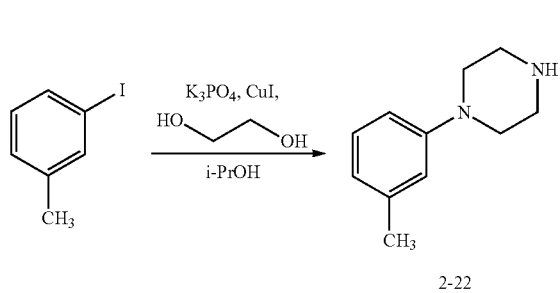

2-22

To a 100 mL round-bottom flask with 25 mL of isopropanol, m-iodotoluene (2.18 g, 0.01 mol) was added, then anhydrous piperazine (1.76 g, 0.02 mol), cuprous iodide (0.5 g, 25 mmol), potassium phosphate (4.66 g, 17.5 mmol) and ethylene glycol (1.5 mL) were added in sequence, and reacted under reflux and argon atmosphere for 18 hours, until TLC (PE:EA=20; 1, DCM:MeOH=10:1) detection showed the reaction was completed. After filtration, the solvent was removed under reduced pressure, 20 mL of water was added, and extraction was carried out with 30 mL of chloroform for three times. The extracts were combined, washed with saturated brine and water, dried over anhydrous sodium sulfate, concentrated to dryness and subjected to column chromatography (EA:MeOH:NH$_3$·H$_2$O=25:3:2) to obtain 0.5 g of a colorless oily product 2-22, yield: 23%.

$^1$H NMR (400 MHz, CDCl$_3$): δ 7.18 (t, J=7.7 Hz, 1H), 6.74 (dd, J=17.8, 8.7 Hz, 3H), 3.14 (s, 8H), 2.35 (s, 3H).

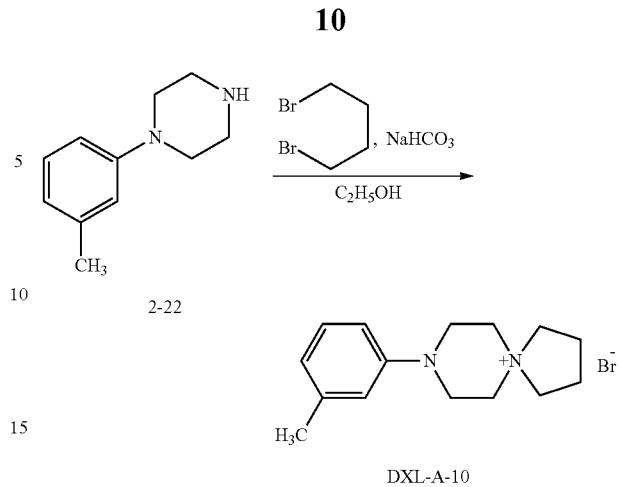

2-22

DXL-A-10

To a 50 mL round-bottom bottle, 18 mL of ethanol was added, and then raw material 3-1 (0.5 g, 2.84 mmol), 1,4-dibromobutane (0.6 g, 2.84 mmol) were added in sequence. NaHCO$_3$ (1.67 g, 19.88 mmol) was taken and ground finely, added to the above system under stirring, heated and reacted under stirring and reflux at 80° C. for 6 hours, and when the TLC detection indicated there was still the raw material, the reaction was continued up to 18 hours. After solid sodium bicarbonate was removed by filtration, the filtrate was evaporated under reduced pressure to give a crude white solid product (0.93 g). 20 mL of ethyl acetate was added to the above solid, sonicated for 5 minutes, filtered to remove ethyl acetate to obtain a crude solid product, which was recrystallized with ethyl acetate/ethanol to give 730 mg of a white solid product, yield: 83%.

General Method II of Synthesis (Taking Compound DXL-A-08 as an example)

2-23   2-24

2-25

To a 250 mL round-bottom flask containing 40 mL of 1,4-dioxane, raw material 2-23 (methyl m-bromobenzoate) (2.15 g, 10 mmol), BINAP (622 mg, 1 mmol), palladium acetate (45 mg, 0.2 mmol), cesium carbonate (6.5 g, 20 mmol), Boc-piperazine 2-24 (1.86 g, 10 mmol) were added in sequence, and reacted under argon atmosphere and reflux at 100° C. for 18 hours, until TLC (PE:EA=10:1) detection showed the reaction was completed. Filtration was carried out with diatomite to remove solid(s). The filtrate was evaporated under reduced pressure and subjected to column chromatography (PE:EA=10:1) to give 720 mg of a light yellow oily product, yield: 23%.

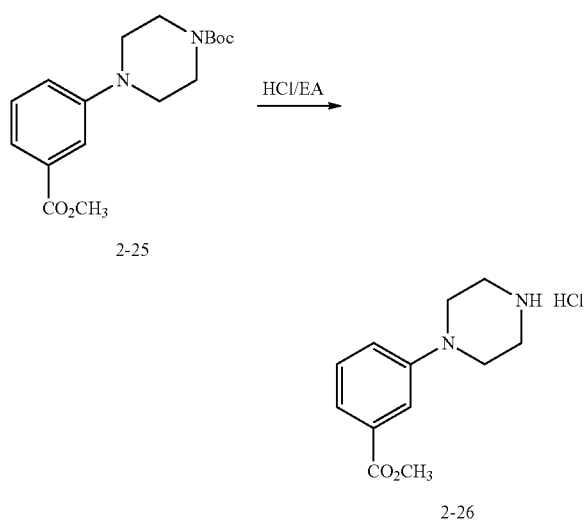

2-25

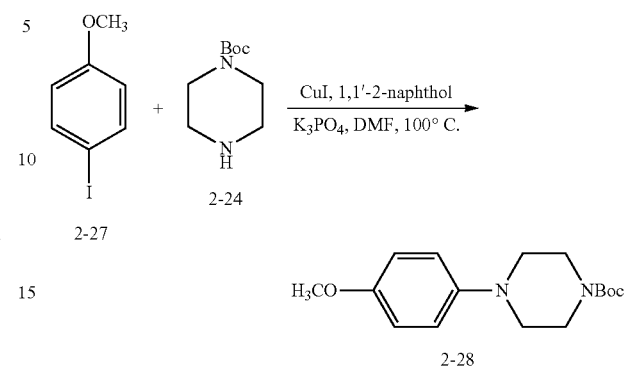

General Method III of Synthesis (Taking Compound DXL-A-26 as an example)

2-27   2-24

2-28

Raw material 2-25 (720 mg, 2.25 mmol) was added into a 50 mL round-bottom bottle, added with hydrochloric acid-ethyl acetate (2.8M), reacted under stirring for 5 hours, and TLC detection showed the reaction of raw material was completed. The product was filtrated to remove hydrochloric acid-ethyl acetate, and washed repeatedly with ethyl acetate until the TLC detection showed that there was only one product spot, and 570 mg of a white solid product 2-26 was obtained. Yield: 99%.

Raw material 4-iodoanisole 2-27 (2.34 g, 10 mmol), ligand (430 mg, 1.5 mmol), CuI (580 mg, 2 mmol), $K_3PO_4$ (5.32 g, 20 mmol) were dissolved in anhydrous DMF (30 mL), then added with Boc-piperazine 2-24 (2.8 g, 15 mmol), reacted under argon atmosphere at 100° C. for 24 hours. TLC detection (PE:EA=5:1) showed the reaction of raw material was completed. Extraction was carried out three times with 50 mL of dichloromethane, and the extracts were combined and washed with saturated sodium chloride solution and water in sequence, and dried over anhydrous sodium sulfate. After column chromatography (PE:EA=5:1), 720 mg of a yellow solid product was obtained. Yield: 24.6%.

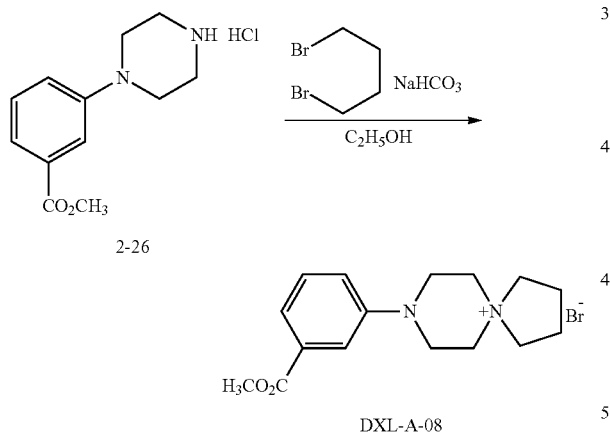

2-26

DXL-A-08

Raw material 2-26 (570 mg, 2.22 mmol) was dissolved in ethanol (15 mL), then added with $NaHCO_3$ (1.5 g, 17.76 mmol) and stirred at room temperature for 10 minutes (to dissociate HCl), then added with 1,4-dibromobutane (527 mg, 2.44 mmol) and reacted at reflux for 6 hours, the TLC detection showed the reaction was completed. After filtration to remove solid $NaHCO_3$, the filtrate was evaporated under reduced pressure, added with 20 mL of ethyl acetate and washed twice. After filtration, a crude white product was obtained, which was recrystallized with ethyl acetate/ethanol to give 160 mg of a white solid product with a yield of 20.3%.

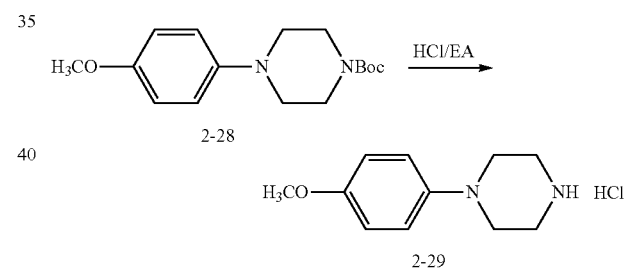

2-28

2-29

Raw material 2-28 (720 mg, 2.46 mmol) was added into a 50 mL round-bottom bottle, then added with hydrochloric acid-ethyl acetate (3.8M), stirred at room temperature for 24 hours, and filtered to obtain 600 mg of a white solid product, yield: 90%.

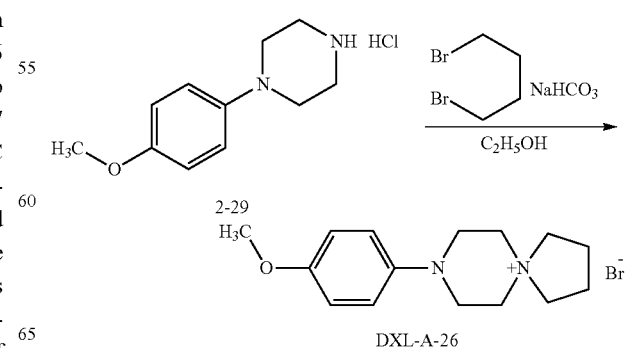

2-29

DXL-A-26

Raw material 2-29 (600 mg, 2.62 mmol) was dissolved in ethanol (15 mL), then added with NaHCO₃ (1.76 g, 20.96 mmol), and then added with 1,4-dibromobutane (567 mg, 2.62 mmol) under stirring. After the reaction was carried out under reflux for 6 hours, TLC detection showed the reaction was completed. NaHCO₃ was removed by filtration, and the solvent was evaporated under reduced pressure to obtain a solid. The resulting solid was washed twice with ethyl acetate (20 mL) and filtered to obtain a solid. The obtained solid was washed twice with dichloromethane under heating, and filtered to obtain a crude solid, which was recrystallized with ethyl acetate/dichloromethane to give 800 mg of a white solid product, yield: 93%.

Example 1

Preparation of DXL-A-16

8-(4-fluorophenyl)-5,8-diazaspiro[4.5]decan-5-ium bromide

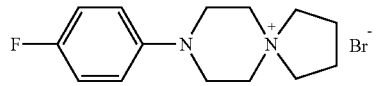

The General Method III was adopted, and a white solid was obtained with a yield of 43%. $^1$H NMR (400 MHz, D₂O) δ 7.24 (d, J=9.0 Hz, 2H), 6.94 (d, J=9.0 Hz, 2H), 3.61-3.26 (m, 12H), 2.10 (s, 4H).

$^{13}$C NMR (101 MHz, D₂O) δ 159.26, 156.89, 145.41, 119.27, 119.19, 116.03, 115.81, 62.66, 59.01, 45.69, 21.08.

ES-HRMS: Calcd for $C_{14}H_{20}BrFN_2$ [M—Br]⁺, 235.31985, Found 235.16041.

Example 2

Preparation of DXL-A-19

8-(4-cyanophenyl)-5,8-diazaspiro[4.5]decan-5-ium bromide

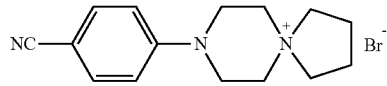

The General method II was adopted, and a white solid was obtained with a yield of 37.1%. $^1$H NMR (400 MHz, D₂O) δ 7.54 (d, J=8.8 Hz, 2H), 6.97 (d, J=8.9 Hz, 2H), 3.54 (dd, J=17.0, 9.7 Hz, 12H), 2.11 (s, 4H).

$^{13}$C NMR (101 MHz, D₂O) δ 152.22, 133.92, 120.55, 115.30, 100.85, 62.52, 58.55, 42.79, 21.03.

ES-HRMS: Calcd for $C_{15}H_{20}BrN_3$ [M—Br]⁺, 242.33885, Found 242.16511.

Example 3

Preparation of DXL-A-21

8-(3,4-difluorophenyl)-5,8-diazaspiro[4.5]decan-5-ium bromide

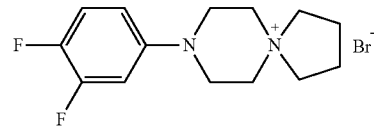

The General Method III was adopted, and a white solid was obtained with a yield of 59.3%. $^1$H NMR (400 MHz, D₂O) δ 7.10 (dd, J=19.3, 9.4 Hz, 1H), 6.89 (m, J=13.1, 6.8, 2.7 Hz, 1H), 6.72 (d, J=8.7 Hz, 1H), 3.69-3.44 (m, 8H), 3.38 (s, 4H), 2.11 (s, 4H).

$^{13}$C NMR (101 MHz, D₂O) δ 151.37, 151.22, 148.93, 148.81, 146.35, 146.22, 146.09, 145.97, 143.96, 143.84, 117.65, 117.48, 113.06, 113.04, 113.01, 112.98, 106.61, 106.41, 62.61, 58.85, 45.08, 21.07.

ES-HRMS: Calcd for $C_{14}H_{19}BrF_2N_2$ [M—Br]⁺, 253.31032, Found 253.15087.

Example 4

Preparation of DXL-A-22

8-(4-bromophenyl)-5,8-diazaspiro[4.5]decan-5-ium bromide

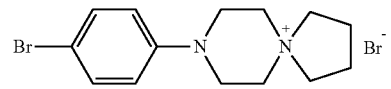

The General Method III was adopted, and a white solid was obtained with a yield of 86.9%. $^1$H NMR (400 MHz, D₂O) δ 7.38 (d, J=8.9 Hz, 2H), 6.89 (d, J=8.9 Hz, 2H), 3.50 (dd, J=12.4, 7.3 Hz, 8H), 3.39 (s, 4H), 2.10 (s, 4H).

$^{13}$C NMR (101 MHz, D₂O) δ 148.30, 132.21, 118.64, 113.20, 62.56, 58.83, 44.37, 21.13.

ES-HRMS: Calcd for $C_{14}H_{20}BR^2N_2$ [M—Br]⁺, 296.22545, Found 296.08329.

DXL-A-22 could also be prepared according to the following method:

1. Preparation of intermediate 4-(4-bromophenyl)-1-Boc-piperazine (C)

Raw material 4-bromoiodobenzene A (10 mmol), 1,1'-di-2-naphthol (430 mg, 1.5 mmol), CuI (580 mg, 2 mmol) and K₃PO₄ (5.32 g, 20 mmol) were dissolved in anhydrous DMF (30 mL), then added with Boc-piperazine B (2.8 g, 15 mmol), and reacted under argon atmosphere at 100° C. for 24 hours. TLC detection (PE:EA=5:1) showed the reaction of raw material was completed. Extraction was carried out for three times with dichloromethane (50 mL×3), the extracts were combined, washed with saturated sodium chloride solution and water in sequence, and dried over anhydrous sodium sulfate. After column chromatography (PE:EA=5:1), 4-(4-bromophenyl)-1-Boc-piperazine C was obtained as a yellow solid product.

2. Preparation of intermediate 1-(4-bromophenyl)piperazine (D)

4-(4-bromophenyl)-1-Boc-piperazine C (2.46 mmol) was added into a 50 mL round-bottom bottle, then added with hydrochloric acid-ethyl acetate (3.8M), stirred at room temperature for 24 hours, and filtered to obtain deprotected intermediate 1-(4-bromophenyl)piperazine (D) as a white solid.

3. Preparation of Ia

The deprotected intermediate 1-(4-bromophenyl)piperazine D (2.62 mmol) was dissolved in ethanol (15 mL), added with NaHCO$_3$ (1.76 g, 20.96 mmol), added with 1,4-dibromobutane (567 mg, 2.62 mmol) under stirring. The reaction was carried out under reflux for 6 hours, and the TLC detection showed the reaction was completed. The NaHCO$_3$ was removed by filtration, and the solvent was evaporated under reduced pressure to obtain a solid. The obtained solid was washed with ethyl acetate and dichloromethane in sequence, and then the obtained crude product was recrystallized with ethyl acetate/dichloromethane to obtain a white solid product Ia with a yield of 86.9%. $^1$H NMR (400 MHz, D$_2$O) δ 7.38 (d, J=8.9 Hz, 2H), 6.89 (d, J=8.9 Hz, 2H), 3.50 (dd, J=12.4, 7.3 Hz, 8H), 3.39 (s, 4H), 2.10 (s, 4H). $^{13}$C NMR (101 MHz, D$_2$O) δ 148.30, 132.21, 118.64, 113.20, 62.56, 58.83, 44.37, 21.13. ES-HRMS: Calcd for C$_{14}$H$_{20}$BR$^2$N$_2$ [M—Br]$^+$, 296.22545, Found 296.08329.

Example 5

Preparation of DXL-A-23

8-(4-chlorophenyl)-5,8-diazaspiro[4.5]decan-5-ium bromide

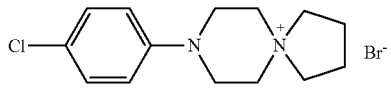

The General Method III was adopted, and a white solid was obtained with a yield of 17.5%. $^1$H NMR (400 MHz, D$_2$O) δ 7.25 (d, J=8.8 Hz, 2H), 6.95 (d, J=8.9 Hz, 2H), 3.51 (dd, J=11.6, 7.1 Hz, 8H), 3.40 (s, 4H), 2.10 (s, 4H).

$^{13}$C NMR (101 MHz, D$_2$O) δ 147.75, 129.23, 125.89, 118.38, 62.56, 58.85, 44.63, 21.08.

ES-HRMS: Calcd for C$_{14}$H$_{20}$BrClN$_2$ [M—Br]$^+$, 251.77445, Found 251.13077.

Example 6

Preparation of DXL-A-24

8-(4-(trifluoromethyl)phenyl)-5,8-diazaspiro[4.5]decan-5-ium bromide

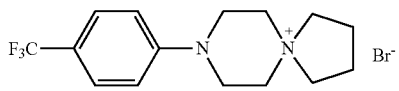

The General Method III was adopted, and a white solid was obtained with a yield of 70.7%. $^1$H NMR (400 MHz, D$_2$O) δ 7.54 (d, J=8.7 Hz, 2H), 7.05 (d, J=8.6 Hz, 2H), 3.52 (d, J=11.3 Hz, 12H), 2.11 (s, 4H).

$^{13}$C NMR (101 MHz, D$_2$O) δ 151.55, 126.66, 126.63, 125.83, 123.15, 121.91, 121.59, 121.25, 115.82, 62.52, 58.68, 43.62, 21.02.

ES-HRMS: Calcd for C$_{15}$H$_{20}$BrF$_3$N$_2$ [M—Br]$^+$, 285.32736, Found 285.15687.

DXL-A-24 could also be prepared according to the following method:

The preparation method was the same as the second preparation method of DXL-A-22 in Example 4, except that A was 4-trifluoromethyl-bromobenzene, and a white solid product Ib was obtained with a yield of 70.7%. $^1$H NMR (400 MHz, D$_2$O) δ 7.54 (d, J=8.7 Hz, 2H), 7.05 (d, J=8.6 Hz, 2H), 3.52 (d, J=11.3 Hz, 12H), 2.11 (s, 4H). $^{13}$C NMR (101 MHz, D$_2$O) δ 151.55, 126.66, 126.63, 125.83, 123.15, 121.91, 121.59, 121.25, 115.82, 62.52, 58.68, 43.62, 21.02. ES-HRMS: Calcd for C$_{15}$H$_{20}$BrF$_3$N$_2$ [M—Br]$^+$, 285.32736, Found 285.15687.

Example 7

Preparation of DXL-A-27

8-(3,5-bis(trifluoromethyl)phenyl)-5,8-diazaspiro[4.5]decan-5-ium bromide

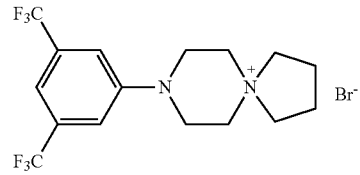

The General Method II was adopted, and a white solid was obtained with a yield of 75%. $^1$H NMR (400 MHz, D$_2$O) δ 7.52 (s, 1H), 7.48 (s, 2H), 3.62 (s, 12H), 2.21 (s, 4H).

$^{13}$C NMR (101 MHz, D$_2$O) δ 149.95, 132.36, 132.03, 131.71, 131.44, 124.86, 122.20, 116.17, 114.18, 114.10, 114.06, 114.02, 62.71, 58.78, 43.86, 21.16.

ES-HRMS: Calcd for C$_{16}$H$_{19}$BrF$_6$N$_2$ [M—Br]$^+$, 353.32533, Found 353.14369.

Example 8

Preparation of DXL-A-28

8-(3-nitro-5-(trifluoromethyl)phenyl)-5,8-diazaspiro[4.5]decan-5-ium bromide

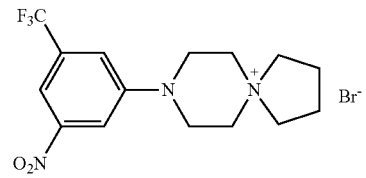

The General Method II was adopted, and a yellow solid was obtained with a yield of 43.2%. $^1$H NMR (400 MHz, D$_2$O) δ 7.88 (d, J=12.1 Hz, 2H), 7.54 (s, 1H), 3.59 (t, J=16.9 Hz, 12H), 2.18 (s, 4H).

$^{13}$C NMR (101 MHz, D$_2$O) δ 150.36, 148.96, 132.63, 132.27, 131.83, 131.49, 124.47, 118.28, 113.33, 111.74, 62.70, 58.66, 43.53, 21.17.

ES-HRMS: Calcd for $C_{15}H_{19}BrF_3N_3O_2$ [M—Br]$^+$, 330.32492, Found 330.14195.

Example 9

Preparation of DXL-A-29

8-(3-methyl-5-nitrophenyl)-5,8-diazaspiro[4.5]decan-5-ium bromide

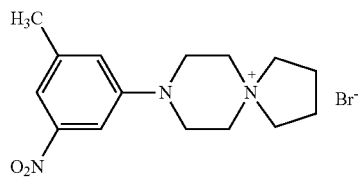

The General Method II was adopted, and a yellow solid was obtained with a yield of 27.1%. $^1$H NMR (400 MHz, D$_2$O) δ 7.50 (s, 2H), 7.20 (s, 1H), 3.79-3.32 (m, 12H), 2.34 (s, 3H), 2.26 (s, 4H).
$^{13}$C NMR (101 MHz, D$_2$O) δ 149.43, 148.38, 123.19, 116.18, 107.69, 62.63, 58.78, 43.99, 21.14, 20.64.
ES-HRMS: Calcd for $C_{15}H_{22}BrN_3O_2$ [M—Br]$^+$, 276.35353, Found 276.17033.

Example 10

Preparation of DXL-A-30

8-(4-methyl-3-nitrophenyl)-5,8-diazaspiro[4.5]decan-5-ium bromide

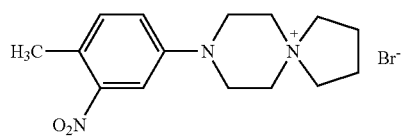

The General Method II was adopted, and a yellow solid was obtained with a yield of 18.2%. $^1$H NMR (400 MHz, D$_2$O) δ 7.31 (s, 1H), 7.10 (t, J=6.6 Hz, 2H), 3.67-3.49 (m, 8H), 3.40 (s, 4H), 2.19 (s, 4H), 2.17 (s, 3H).
$^{13}$C NMR (101 MHz, D$_2$O) δ 148.67, 147.64, 133.68, 126.13, 121.81, 111.63, 62.70, 58.87, 44.16, 21.18, 18.78.
ES-HRMS: Calcd for $C_{15}H_{22}BrN_3O_2$ [M—Br]$^+$, 276.35353, Found 276.17085.

Example 11

Preparation of DXL-A-32

8-(4-cyano-3-nitrophenyl)-5,8-diazaspiro[4.5]decan-5-ium bromide

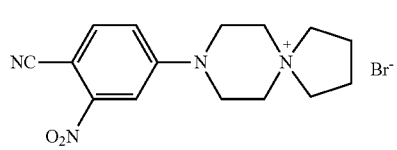

The General Method II was adopted, and a yellow solid was obtained with a yield of 32.6%. $^1$H NMR (400 MHz, D$_2$O) δ 7.58 (dd, J=10.9, 5.5 Hz, 2H), 7.14 (dt, J=33.4, 16.7 Hz, 1H), 3.73 (s, 4H), 3.66-3.51 (m, 8H), 2.16 (s, 4H).
$^{13}$C NMR (101 MHz, D$_2$O) δ 152.27, 136.61, 118.50, 117.34, 110.52, 94.25, 62.60, 58.29, 42.14, 21.05.
ES-HRMS: Calcd for $C_{15}H_{19}BrN_4O_2$ [M—Br]$^+$, 287.33641, Found 287.15134.

Example 12

Preparation of DXL-A-05

8-(3-chlorophenyl)-5,8-diazaspiro[4.5]decan-5-ium bromide

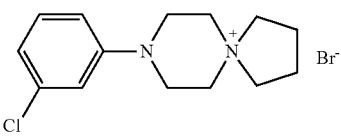

The General Method III was adopted, and a white solid was obtained with a yield of 58.8%. $^1$H NMR (400 MHz, D$_2$O) δ 7.23 (d, J=8.1 Hz, 1H), 7.01 (d, J=1.8 Hz, 1H), 6.92 (dd, J=17.4, 8.1 Hz, 2H), 3.47 (dd, J=30.2, 26.7 Hz, 12H), 2.14 (s, 4H).
$^{13}$C NMR (101 MHz, D$_2$O) δ 150.24, 134.62, 130.77, 121.34, 116.65, 115.14, 62.62, 58.81, 44.36, 21.09.
ES-HRMS: Calcd for $C_{14}H_{20}BrClN_2$ [M—Br]$^+$, 251.77445, Found 251.13082.

Example 13

Preparation of DXL-A-06

8-(3-(trifluoromethyl)phenyl)-5,8-diazaspiro[4.5]decan-5-ium bromide

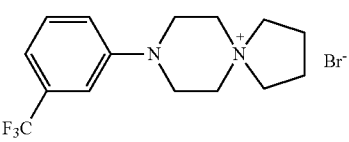

The General Method II was adopted, and a white solid was obtained with a yield of 23.7%. $^1$H NMR (400 MHz, D$_2$O) δ 7.46 (t, J=7.9 Hz, 1H), 7.31 (s, 1H), 7.26 (t, J=7.6 Hz, 2H), 3.58 (dd, J=13.8, 5.7 Hz, 12H), 2.17 (s, 4H).
$^{13}$C NMR (101 MHz, D$_2$O) δ 149.37, 131.22, 130.90, 130.29, 125.46, 122.77, 120.24, 117.94, 113.20, 62.65, 58.87, 44.39, 21.11.
ES-HRMS: Calcd for $C_{15}H_{20}BrF_3N_2$ [M—Br]$^+$, 285.32736, Found 285.15715.

Example 14

Preparation of DXL-A-10

8-(m-tolyl)-5,8-diazaspiro[4.5]decan-5-ium bromide

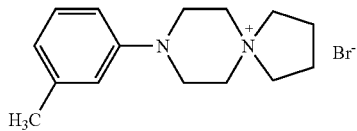

The General Method I was adopted, and a white solid was obtained with a yield of 83%. $^1$H NMR (400 MHz, D$_2$O) δ 7.22 (t, J=7.8 Hz, 1H), 6.90 (s, 1H), 6.85 (d, J=6.8 Hz, 2H), 3.62-3.49 (m, 8H), 3.44 (s, 4H), 2.24 (s, 3H), 2.15 (s, 4H).

$^{13}$C NMR (101 MHz, D$_2$O) δ 160.00, 150.52, 130.67, 110.01, 107.15, 103.40, 62.61, 58.90, 55.44, 44.80, 21.07.

ES-HRMS: Calcd for C$_{15}$H$_{23}$BrN$_2$ [M—Br]$^+$, 231.35597, Found 231.18548.

Example 15

Preparation of DXL-A-18

8-(2-fluorophenyl)-5,8-diazaspiro[4.5]decan-5-ium bromide

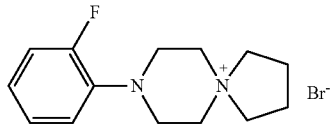

The General Method III was adopted, and a white flake crystal was obtained with a yield of 91%. $^1$H NMR (400 MHz, D$_2$O) δ 7.15-6.98 (m, 4H), 3.63-3.43 (m, 8H), 3.31 (s, 4H), 2.11 (s, 4H).

$^{13}$C NMR (101 MHz, D$_2$O) δ 156.72, 154.51, 137.09, 137.00, 125.09, 125.05, 125.02, 119.84, 116.47, 116.27, 62.82, 59.20, 45.73, 21.03.

ES-HRMS: Calcd for C$_{14}$H$_{20}$BrFN$_2$ [M—Br]$^+$, 235.31985, Found 235.16094.

EFFECT EXAMPLES

For the preparation of compounds LXM-21, LXM-22, see WO 2007/147346 A1, which is incorporated by reference in its entirety.

Each compound was administrated at doses of 0.4, 1, 3, 4, 6, 9, and 12 mg/kg, and when there was no significant difference in the efficacy of each compound administered at a lower dose, a successively increased dose was used, that was, when the dose of 0.4 mg/kg showed no significant difference in comparison with the control, the dose would be adjusted to 1 mg/kg for repeating the test, and so on.

Because the molecular weights of compounds DXL-A-27, DXL-A-28, DXL-A-29, DXL-A-30, DXL-A-32 were quite different from those of other compounds, the doses of these compounds were all 4 µmol/kg.

Experimental Animals

ICR mice, 18-22 g, half of them being male and the other half being female, provided by the Department of Laboratory Animals, Peking University (License No.: SCXK (Beijing) 2016-0010).

The analgesic effects of the compounds of the present invention were measured using the following experiments.

The following examples related to the pharmaceutical experiments of the compounds of the present invention. In the following experiments, all results of the pharmaceutical experiments were statistically processed, and the experimental results were analyzed using SPSS 13.0 software; in the acetic acid writhing test and the formalin experiment, one-way analysis of variance was used for comparison between the groups; in the hot plate test and the xylene-induced mouse ear swelling test, repeated measures analysis of variance was used, and the significance test standard was $P<0.05$.

Effect Example 1: Hot Plate Test

The temperature of hot plate was adjusted to 55° C., and the responses of mouse such as licking hind feet and jumping were used as the observation indexes. The time from the placement of mice on copper plate to the appearance of the above responses was defined as latency time. The latency time was measured for three times 30 minutes before administration, and the average value thereof was used as basic threshold, or baseline latency (BL). The animals with a latency time greater than 15 s and less than 5 s were removed, and the residual mice were randomly grouped, 8 animals per group. Vehicle control group (double-distilled water) and groups for samples to be tested (the compounds and doses thereof were shown in Table 1) were set. All drugs were dissolved in normal saline before administration, and given by intragastric administration. The latency time was measured 2.0 hours after administration. Percentage of Pain Threshold Elevated Rate (PTE %) of compound on mice was calculated according to the following formula:

PTE %=(latency time of test group−latency time of vehicle control group)/latency time of vehicle control group×100

The experimental results were shown in Table 1 below. The results of the compounds of the present invention showed $P<0.05$ as compared to the vehicle group, in which the compounds DXL-A-16, DXL-A-19, DXL-A-21, DXL-A-22, DXL-A-23, DXL-A-24, DXL-A-27, DXL-A-28, DXL-A-29 and DXL-A-32 showed $P<0.01$ as compared to the solvent group.

TABLE 1

Pain Threshold Elevated Rates of the compounds of the present invention

| Compound | Dose | PTE % |
|---|---|---|
| Vehicle control (double-distilled water) | — | 0 |
| LXM-21 | 3 mg/kg | 4.78 |
| LXM-22 | 3 mg/kg | 25.03 |
| DXL-A-05 | 3 mg/kg | 19.5 |
| DXL-A-06 | 3 mg/kg | 16.67 |
| DXL-A-10 | 3 mg/kg | 11.18 |
| DXL-A-16 | 1 mg/kg | 31.44 |
| DXL-A-19 | 1 mg/kg | 34.34 |
| DXL-A-21 | 1 mg/kg | 36.63 |
| DXL-A-22 | 1 mg/kg | 52.57 |
| DXL-A-23 | 1 mg/kg | 39.24 |
| DXL-A-24 | 1 mg/kg | 48.64 |

TABLE 1-continued

Pain Threshold Elevated Rates of the compounds of the present invention

| Compound | Dose | PTE % |
|---|---|---|
| DXL-A-27 | 4 μmol/kg | 49 |
| DXL-A-28 | 4 μmol/kg | 36 |
| DXL-A-29 | 4 μmol/kg | 36 |
| DXL-A-30 | 4 μmol/kg | 21 |
| DXL-A-32 | 4 μmol/kg | 38 |

Effect Example 2: Acetic Acid Writhing Test

ICR mice, half of them being male and the other half being female, were randomly grouped, 8 mice per group. Vehicle control group (double-distilled water), ibuprofen control group, and groups for samples to be tested (the compounds and doses thereof were shown in Table 2) were set. All drugs were dissolved in double-distilled water before administration, and given by intragastric administration at predetermined doses. Two hours after the administration, the mice were intraperitoneally injected with 0.6% acetic acid solution (10 ml/kg, ip), and the number of times the mice writhed (abdomen depressed, buttock raised, body elongated) was recorded within 5-20 minutes. The inhibition rate % of compound on writhing pain in mice was calculated according to the following formula.

Inhibition rate %=(number of writhing times in vehicle control group−number of writhing times in test group)/number of writhing times in vehicle control group×100

The analgesic effects of the compounds of the present invention on acetic acid-stimulated pain were shown in Table 2. The results of the compounds of the present invention showed P<0.05 as compared to the vehicle control group, in which the compounds DXL-A-29 and DXL-A-30 showed P<0.01 as compared to the vehicle control group.

TABLE 2

Analgesic effects of the compounds of the present invention on acetic acid-induced pain

| Compound | Dose | Inhibition rate (%) |
|---|---|---|
| Vehicle control (double-distilled water) | — | 0 |
| LXM-21 | 3 mg/kg | 32.45 |
| LXM-22 | 3 mg/kg | 16.4 |
| DXL-A-05 | 3 mg/kg | 22.49 |
| DXL-A-06 | 3 mg/kg | 14.03 |
| DXL-A-10 | 3 mg/kg | 29.82 |
| DXL-A-16 | 1 mg/kg | — |
| DXL-A-18 | 1 mg/kg | 21.71 |
| DXL-A-19 | 1 mg/kg | — |
| DXL-A-21 | 1 mg/kg | — |
| DXL-A-22 | 1 mg/kg | — |
| DXL-A-23 | 1 mg/kg | — |
| DXL-A-24 | 1 mg/kg | — |
| DXL-A-27 | 4 μmol/kg | — |
| DXL-A-28 | 4 μmol/kg | — |
| DXL-A-29 | 4 μmol/kg | 75.97 |
| DXL-A-30 | 4 μmol/kg | 41.75 |
| DXL-A-32 | 4 μmol/kg | — |
| Ibuprofen table | 200 mg/kg | 49.08 |

Note:
Symbol "—" indicates that the data obtained at this dose was not significantly different from the vehicle control group.

Effect Example 3: Formalin Experiment

ICR mice, half of them being male and the other half being female, were randomly grouped, 8 mice per group. Vehicle control group (double-distilled water) and groups for samples to be tested were set, in which the compounds and doses thereof were shown in Table 3. All drugs were dissolved in double-distilled water before administration, and given by intragastric administration at predetermined doses. Two hours after administration, the mice were injected with 20 ul of 2.5% formalin solution in the right hind foot, and the time (s) of licking or biting foot was recorded as an index of pain response, in which 0-5 minutes was phase I, 10-60 minutes was phase II, and the total observation time was 60 minutes. The phase II pain inhibition rate of compound in mice was calculated according to the following formula:

Inhibition rate %=(time of licking or biting foot in vehicle control group−time of licking or biting foot in test group)/time of licking or biting foot in vehicle control group×100

The effects of the compounds of the present invention on formalin-stimulated pain were shown in Table 3. The results of the compounds of the present invention showed P<0.05 as compared to the vehicle control group, in which the compounds DXL-A-05, DXL-A-10, DXL-A-16, DXL-A-19, DXL-A-21, DXL-A-22, DXL-A-23 and DXL-A-24 showed P<0.01 as compared to the vehicle group.

TABLE 3

Effect of the compounds of the present invention on formalin-stimulated pain

| Compound | Dose | Phase II pain inhibition rate (%) |
|---|---|---|
| Vehicle control (double-distilled water) | — | 0 |
| LXM-21 | 9 mg/kg | 42.01 |
| LXM-22 | 9 mg/kg | 19.28 |
| DXL-A-05 | 9 mg/kg | 32.93 |
| DXL-A-06 | 9 mg/kg | 17.62 |
| DXL-A-10 | 9 mg/kg | 46.93 |
| DXL-A-16 | 1 mg/kg | 31.44 |
| DXL-A-18 | 1 mg/kg | 21.99 |
| DXL-A-19 | 1 mg/kg | 34.34 |
| DXL-A-21 | 1 mg/kg | 36.63 |
| DXL-A-22 | 1 mg/kg | 52.57 |
| DXL-A-23 | 1 mg/kg | 39.24 |
| DXL-A-24 | 1 mg/kg | 50.17 |
| DXL-A-27 | 4 μmol/kg | 20.07 |
| DXL-A-28 | 4 μmol/kg | 13.35 |
| DXL-A-29 | 4 μmol/kg | 17.29 |
| DXL-A-30 | 4 μmol/kg | 16.92 |
| DXL-A-32 | 4 μmol/kg | 2.64 |

Effect Example 4: Xylene-Induced Mouse Ear Swelling Test

ICR mice were randomly grouped, 8 mice per group, half of them being male and the other half being female. Vehicle control group (double-distilled water) and groups for samples to be tested (the compounds and doses thereof were shown in Table 4). All drugs were dissolved in double-distilled water immediately before administration, and given by intragastric administration at predetermined doses. Two hours after administration, 50 uL of xylene was smeared evenly on the inner and outer sides of right ear of mouse. After 30 minutes, the left and right ears of mouse were cut, and circular ear pieces of the same size were punched at the same position on the left and right ears, and weighed. The ear swelling inhibition rate of compound in mice was calculated according to the formula.

Inhibition rate %=(degree of ear swelling in vehicle control group−degree of ear swelling in test group)/degree of ear swelling in vehicle control group×100

The effects of the compounds of the present invention on xylene-induced ear swelling in mice were shown in Table 4. The results of the compounds of the present invention showed P<0.05 as compared with the vehicle control group, in which the compounds DXL-A-05, DXL-A-06, DXL-A-21, DXL-A-22, DXL-A-24 and DXL-A-29 showed P<0.01 as compared to the vehicle control group.

TABLE 4

Effects of the compounds of the present invention on xylene-induced ear swelling in mice

| Compound | Dose | Inhibition rate (%) |
| --- | --- | --- |
| Vehicle control (double-distilled water) | — | 0 |
| LXM-21 | 3 mg/kg | 10.85 |
| LXM-22 | 3 mg/kg | — |
| DXL-A-05 | 3 mg/kg | 30.81 |
| DXL-A-06 | 3 mg/kg | 45.85 |
| DXL-A-10 | 3 mg/kg | 27.37 |
| DXL-A-16 | 1 mg/kg | — |
| DXL-A-18 | 1 mg/kg | — |
| DXL-A-19 | 1 mg/kg | — |
| DXL-A-21 | 1 mg/kg | 42.46 |
| DXL-A-22 | 1 mg/kg | 46.97 |
| DXL-A-23 | 1 mg/kg | — |
| DXL-A-24 | 1 mg/kg | 53.37 |
| DXL-A-27 | 4 μmol/kg | 4.13 |
| DXL-A-28 | 4 μmol/kg | 9.27 |
| DXL-A-29 | 4 μmol/kg | 63.27 |
| DXL-A-30 | 4 μmol/kg | — |
| DXL-A-32 | 4 μmol/kg | 20.37 |

Note:
Symbol "—" indicates that the data obtained at this dose was not significantly different from the vehicle control group.

Effect Example 5: Study on Anti-Neuropathic Pain Effects of Compounds DXL-A-22 and DXL-A-24

Materials and Method
1 Materials
1.1 Animals

SD rats, body weight 180 g-220 g, half of them being male and the other half being female, provided by the Department of Laboratory Animals, Peking University. The rats were raised in a standard environment with temperature of 22±0.5° C. and relative humidity of 55±5%, 12 h/12 h light-dark cycle, and fed with standard feed.

1.2 Reagents

Compound DXL-A-22 and Compound DXL-A-24, provided by the Department of Chemical Biology, Peking University; Gabapentin (Jiangsu Hengrui Pharmaceutical Co., Ltd.)

1.3 Instruments von Frey electronic pain tester (IITC 2390, USA); thermal pain response tester (LE 7406, USA)

2 Method
2.1 Model of Chronic Compressive Injury of Sciatic Nerve (CCI)

Rat was anesthetized with pentobarbital sodium (60 mg/kg, i.p.), the right hind limb was surgically shaved, fixed in the prone position, a longitudinal incision was made along the middle of the right hind limb of the rat, the muscle was bluntly separated, the sciatic nerve was exposed, and the sciatic nerve bifurcate proximal end was loosely ligated with 4-0 silk suture for 4 times, with an interval of about 1 mm each time, in which the degree of tightness was suitable when it was observed that the right hind leg was slightly shaken. After ligation, the muscle and skin were sutured in sequence. For the sham-operated group, the sciatic nerve was only exposed, but not ligated. The success of modeling was determined by observing whether the hind limb of the rat's operation side was closed, slightly valgus and often vacated, and by measuring the mechanical stimulation paw withdrawal threshold and the thermal stimulation paw withdrawal latency of the rat.

Before surgery, the mechanical stimulation paw withdrawal thresholds and the thermal stimulation paw withdrawal latencies in the rats were determined, and the rats were grouped as: sham operation group (sham), vehicle group (double-distilled water, i.g.), DXL-A-22 group (2 mg/kg, i.g.), DXL-A-24 group (1 mg/kg, i.g.), and Gabapentin group (100 mg/kg, i.g.). All compounds and drugs were dissolved in double-distilled water, and given by intragastric administration at 1 mL/100 g. From the first day after surgery, the administration was carried out every day, and the mechanical stimulation paw withdrawal threshold and the thermal stimulation paw withdrawal latency were measured 2 hours after administration.

2.2 Determination of Mechanical Stimulation Paw Withdrawal Threshold (MWT)

The mechanical stimulation paw withdrawal threshold (MWT) of rats was detected by von Frey electronic pain tester. The measurement was carried out on the days 5, 7 and 14 after operation. The rats were placed in a transparent plexiglass box (whose bottom was a wire mesh with a gap of 1 mm$^2$) to adapt to the environment for 30 min. After the rats had no exploration action, the von Frey electronic pain tester was used to stimulate the middle position of paw at the operation side of the rat, and the maximum force caused by rat paw withdrawal response (i.e., MWT) was recorded. The inhibition rate of the compound was calculated according to the following formula:

Absolute increase rate (i.e., PTE %): PTE %=(MWT of test group−MWT of vehicle group)/MWT of vehicle group×100   (1)

Relative increase rate: Inhibition rate %=(MWT of test group−MWT of vehicle group)/(MWT of Sham operation group−MWT of vehicle group)×100   (2)

2.3 Determination of Thermally Stimulation Paw Withdrawal Latency (PWL)

The thermal stimulation paw withdrawal latency (PWL) was measured by a hot plate method. The measurement was carried out on the days 5, 7 and 14 after operation. The temperature of the hot plate was 50.5° C. Timing started when the rat was placed on the hot plate, and stopped when the shaking and foot licking responses of the rat appeared, and this time was the PWL of the rat. The hot plate cut-off time was 14s, and the percentage of analgesia (i.e., MPE %) was calculated according to formula (3):

MPE %=(PWL of test group−PWL of vehicle group)/(cut-off time−PWL of vehicle group)×100   (3)

2.4 Statistical Processing

The results were expressed in mean±SEM, and SPSS 19.0 software was used for analysis. Repeated measures analysis of variance was used for the comparison between the groups in the mechanical stimulation test and for the comparison between the groups in the thermal stimulation test. The significance test standard was P<0.05.

3 Experimental Results 3.1 Effects of DXL-A-22 on Mechanical Stimulation Paw Withdrawal Threshold (MWT) in CCI Rats (mean±SEM, n=8)

| Group | Dose (mg/kg) | MWT/inhibition rate (absolute %/relative %) | | |
|---|---|---|---|---|
| | | Day 5 after operation | Day 7 after operation | Day 14 after operation |
| Sham operation group | — | 37.92 ± 1.67** | 37.87 ± 0.67** | 38.41 ± 1.93** |
| Vehicle group | — | 10.90 ± 1.23 | 10.22 ± 0.84 | 10.56 ± 1.32 |
| DXL-A-22 | 2 | 19.28 ± 1.44**/ (76.88/31.01) | 22.16 ± 0.79**/ (116.83/43.18) | 22.05 ± 0.74**/ (108.81/41.26) |
| Gabapentin | 100 | 21.73 ± 0.49**/ (99.36/40.08) | 23.37 ± 1.34**/ (128.67/47.56) | 21.27 ± 0.82**/ (101.42/38.46) |

**$P < 0.01$, as compared with the vehicle group.

3.2 Effects of DXL-A-22 on Thermal Stimulation Paw Withdrawal Latency (PWL) in CCI Rats (mean±SEM, n=8)

| Group | Dose (mg/kg) | PWL/MPE(%) | | |
|---|---|---|---|---|
| | | Day 5 after operation | Day 7 after operation | Day 14 after operation |
| Sham operation group | — | 11.34 ± 0.46** | 11.77 ± 0.67** | 11.45 ± 0.47** |
| Vehicle group | — | 7.47 ± 0.43 | 7.38 ± 0.19 | 7.67 ± 0.23 |
| DXL-A-22 | 2 | 10.84 ± 0.32**/ 51.61 | 11.28 ± 0.64**/ 58.91 | 11.19 ± 0.52**/ 55.61 |
| Gabapentin | 100 | 11.37 ± 0.32**/ 59.72 | 11.76 ± 0.34**/ 66.16 | 11.88 ± 0.40**/ 66.51 |

**$P < 0.01$, as compared with the vehicle group.

3.3 Effects of DXL-A-24 on Mechanical Stimulation Paw Withdrawal Threshold (MWT) in CCI Rats (mean±SEM, n=8)

| Group | Dose (mg/kg) | MWT/inhibition rate (absolute %/relative %) | | |
|---|---|---|---|---|
| | | Day 5 after operation | Day 7 after operation | Day 14 after operation |
| Sham operation group | — | 36.34 ± 1.82 | 36.29 ± 1.16 | 37.80 ± 1.90 |
| Vehicle group | — | 11.56 ± 1.24 | 10.48 ± 0.78 | 11.60 ± 0.97 |
| DXL-A-24 | 1 | 20.32 ± 1.09**/ (75.78/35.35) | 22.84 ± 1.64**/ (117.94/47.89) | 20.31 ± 1.57**/ (75.09/33.24) |
| Gabapentin | 100 | 21.73 ± 0.49**/ (87.98/41.04) | 23.37 ± 1.34**/ (123.00/49.94) | 21.27 ± 0.82**/ (83.36/36.91) |

**$P < 0.01$, as compared with the vehicle group.

3.4 Effects of DXL-A-24 on Thermal Stimulation Paw Withdrawal Latency (PWL) in CCI Rats (mean±SEM, n=8)

| Group | Dose (mg/kg) | PWL/MPE(%) | | |
|---|---|---|---|---|
| | | Day 5 after operation | Day 7 after operation | Day 14 after operation |
| Sham operation group | — | 12.43 ± 0.55** | 12.47 ± 0.48** | 13.17 ± 0.25** |
| Vehicle group | — | 8.28 ± 0.67 | 8.03 ± 0.49 | 7.40 ± 0.37 |
| DXL-A-24 | 1 | 11.29 ± 0.57**/ 52.62 | 12.35 ± 0.55**/ 72.36 | 13.26 ± 0.43**/ 88.79 |
| Gabapentin | 100 | 11.37 ± 0.32**/ 54.02 | 11.76 ± 0.34**/ 62.48 | 11.88 ± 0.40**/ 67.88 |

**$P < 0.01$, as compared with the vehicle group.

Effect Example 6: Study on Anti-Inflammatory Effects of Compounds DXL-A-22 and DXL-A-24

1 Materials 1.1 Animals

ICR mice, body weight 18 g-22 g, half of them being male and the other half being female, provided by the Department of Laboratory Animals, Peking University. The animals were raised in a standard environment: temperature 23±1° C., relative humidity 55±5%, light-dark cycle 12 h/12 h, and fed with standard pellet feed.

1.2 Reagents

Compounds DXL-A-22 and DXL-A-24 were synthesized and provided by the Department of Chemical Biology, Peking University; dexamethasone acetate tablets (Zhejiang Xianju Pharmaceutical Co., Ltd., batch number: 120415); xylene (Beijing Chemical Plant, batch number: 20100513); carrageenan (Sigma-Adlrich Company of USA, batch number: 015K0172).

1.3 Instruments

Self-made hole punch (6 mm diameter). YLS-7B plantar volume meter, Equipment Station of Shandong Academy of Medical Sciences.

2 Method 2.1 Xylene-Induced Ear Swelling Test in Mice

Mice were randomly divided into 5 groups, 8 mice per group, half of them being male and the other half being female. Vehicle control group (double-distilled water, i.g.), dexamethasone control group (2 mg/kg, i.g.), compound DXL-A-22 group (1 mg/kg, i.g.), and compound DXL-A-24 group (1 mg/kg, i.g.) were set. All drugs were dissolved in double-distilled water before administration, and given by intragastric administration at 0.1 mL/10 g. One hour after administration, 30 µL of xylene was evenly smeared on the inner and outer sides of right ear of mouse to cause inflammation. After 0.5 hour, the left and right ears of mouse were cut, and circular ear pieces of the same size were punched at the same position on the left and right ears using the punch (diameter 6 mm) respectively, and weighed for the weights of the left and right ear pieces. The difference between the weight of the right ear after applying xylene and the weight of the left ear without applying xylene was used as swelling degree index (i.e., swelling degree). The swelling degree was calculated according to formula (1). The intensity of anti-inflammatory effect was expressed as inhibition rate (%), and the inhibition rate (%) was calculated according to formula (2).

Swelling degree=weight of right ear piece−weight of left ear piece     (1)

Inflammation inhibition rate (%)=(ear swelling degree in vehicle control group−ear swelling degree in drug group)/ear swelling degree in vehicle control group×100%     (2)

2.2 Carrageenan-Induced Paw Swelling in Mice

The mouse was fixed in a special holder, and both hind feet were exposed. Before the test, a line was drawn at 0.5 cm below the ankle joint of mouse with a marker, and used as a mark for measuring plantar volume. 30 minutes before administration the volume of right hind foot was measured as basic threshold. The mice were randomly divided into 5 groups, 8 mice per group, half of them being male and the other half being female. Vehicle control group (double-distilled water, i.g.), dexamethasone control group (0.5 mg/kg, i.g.), compound DXL-A-22 group (1 mg/kg, i.g.), and DXL-A-24 group (1 mg/kg, i.g.) were set. All drugs were dissolved in double-distilled water before administration, and were administered at 0.1 mL/10 g. Immediately after intragastric administration, 20 μL of 5% carrageenan saline solution was injected subcutaneously in the right hind foot of the mice, and the plantar volumes were measured at time points of 0.5 h, 1 h and 2 h after injection. The difference between the plantar volume of right foot after injection of carrageenan and the plantar volume of right foot before injection was used as swelling degree index (i.e., swelling degree). The swelling degree was calculated according to formula (3). The intensity of anti-inflammatory effect was expressed as inhibition rate (%), and the inhibition rate (%) was calculated according to formula (4).

Swelling degree=plantar volume of right foot after injection–plantar volume of right foot before injection (3)

Inflammation inhibition rate (%)=(plantar swelling degree in vehicle control group–plantar swelling degree in drug administration group)/plantar swelling degree in vehicle control group×100% (4)

2.3 Statistical Processing

The results were expressed as mean±SD. SPSS 19.0 software was used for analysis. One-way analysis of variance was used for the comparison between the groups in the xylene-induced mouse ear swelling test; and repeated measures analysis of variance was used for the comparison between the groups in the carrageenan-induced mouse plantar swelling test. The significance test standard was $P<0.05$.

3. Experimental Results

3.1 Effects of Compounds DXL-A-22 and DXL-A-24 on Xylene-Induced Ear Swelling in Mice (mean±SD, n=8)

| Group | Dose (mg/kg) | Swelling degree (mg) | Inhibition rate (%) |
|---|---|---|---|
| Vehicle control | — | 9.55 ± 0.34 | — |
| Dexamethasone | 2 | 2.93 ± 0.32** | 69.28 |
| DXL-A-22 | 1 | 5.48 ± 0.16** | 42.62 |
| DXL-A-24 | 1 | 4.64 ± 0.11** | 51.41 |

**$P < 0.01$, as compared with the vehicle control group.

3.2 Effects of Compounds DXL-A-22 and DXL-A-24 on Carrageenan-Induced Plantar Swelling in Mice (mean±SD, n=8)

| Group | Dose (mg/kg) | 0.5 h swelling degree (μL)/ inhibition rate (%) | 1 h swelling degree (μL)/ inhibition rate (%) | 2 h swelling degree (μL)/ inhibition rate (%) |
|---|---|---|---|---|
| Vehicle control | — | 85.38 ± 19.81 | 86.63 ± 28.32 | 111.50 ± 25.88 |
| Dexamethasone | 0.5 | 26.00 ± 14.21**/ 69.55 | 19.88 ± 10.09**/ 77.06 | 17.13 ± 11.54**/ 84.64 |
| DXL-A-22 | 1 | 42.63 ± 16.98**/ 50.07 | 38.50 ± 11.40**/ 55.56 | 38.63 ± 11.67**/ 65.36 |
| DXL-A-24 | 1 | 40.75 ± 13.34**/ 52.27 | 36.63 ± 16.12**/ 57.72 | 36.25 ± 9.60**/ 67.49 |

**$P < 0.01$, as compared with the vehicle control group at the same time.

From the above results, we can conclude that the compounds of the present invention are a class of compounds with obvious analgesic effects, and are expected to be developed into a new generation of analgesic drugs.

What is claimed is:

1. A compound represented by the Formula (II), or a stereoisomer, tautomer, prodrug, or pharmaceutically acceptable salt thereof:

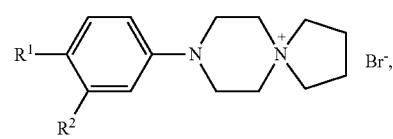

(II)

wherein $R^1$ is selected from the group consisting of hydrogen, fluorine, bromine, cyano and haloalkyl, $R^2$ is selected from the group consisting of hydrogen, halogen, alkyl and nitro, and $R^1$ and $R^2$ are not hydrogen at the same time;

and when $R^2$ is nitro or halogen, $R^1$ is not hydrogen.

2. The compound according to claim 1, or a stereoisomer, tautomer, prodrug, or pharmaceutically acceptable salt thereof, wherein the compound is represented by Formula (II):

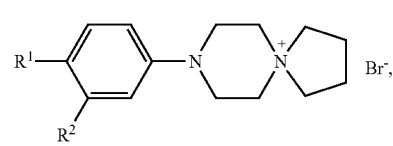

(II)

wherein $R^1$ is fluorine, bromine or haloalkyl; $R^2$ is hydrogen or nitro.

3. The compound according to claim 1, or a stereoisomer, tautomer, prodrug or pharmaceutically acceptable salt thereof, wherein $R^1$ is cyano, fluorine, bromine or haloalkyl, and $R^2$ is hydrogen.

4. The compound according to claim 1, or a stereoisomer, tautomer, prodrug, or pharmaceutically acceptable salt thereof, wherein $R^1$ is fluorine, bromine or haloalkyl, and $R^2$ is hydrogen.

5. The compound, or a stereoisomer, tautomer, prodrug, or pharmaceutically acceptable salt thereof, wherein the compound is selected from the group consisting of:

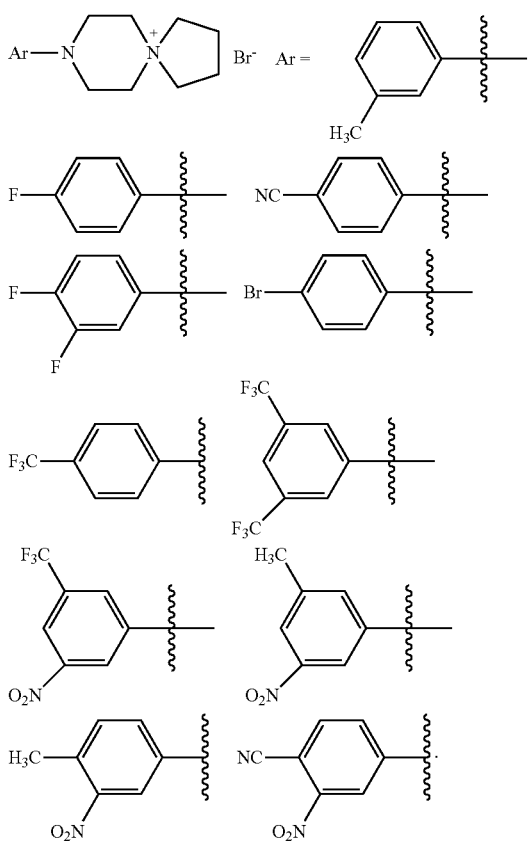

6. A pharmaceutical composition, the pharmaceutical composition comprising the compound according to claim 1, or a stereoisomer, tautomer, prodrug, or pharmaceutically acceptable salt thereof, and optionally a pharmaceutically acceptable carrier.

7. A pharmaceutical composition, the pharmaceutical composition comprising the compound according to claim 5, or a stereoisomer, tautomer, prodrug, or pharmaceutically acceptable salt thereof, and optionally a pharmaceutically acceptable carrier.

8. A method for relieving a pain or combating an inflammation, the method comprising administrating the compound according to claim 1, or a stereoisomer, tautomer, prodrug, or pharmaceutically acceptable salt thereof to a subject in need thereof.

9. A method for relieving a pain or combating an inflammation, the method comprising administering the compound according to claim 5, or a stereoisomer, tautomer, prodrug, or pharmaceutically acceptable salt thereof to a subject in need thereof.

10. The compound according to claim 1, or a stereoisomer, tautomer, prodrug, or pharmaceutically acceptable salt thereof, wherein $R^2$ is alkyl, and $R^1$ is hydrogen.

11. The compound according to claim 1, or a stereoisomer, tautomer, prodrug, or pharmaceutically acceptable salt thereof, wherein $R^2$ is methyl or ethyl, and $R^1$ is hydrogen.

12. The compound according to claim 1, or a stereoisomer, tautomer, prodrug, or pharmaceutically acceptable salt thereof, wherein $R^1$ is selected from the group consisting of fluorine, bromine, cyano and haloalkyl, and $R^2$ is selected from the group consisting of halogen, alkyl, and nitro.

13. The compound according to claim 1, or a stereoisomer, tautomer, prodrug, or pharmaceutically acceptable salt thereof, wherein $R^1$ is selected from the group consisting of fluorine, bromine, cyano and trifluoromethyl, and $R^2$ is selected from the group consisting of fluorine, chlorine, bromine, methyl, ethyl, and nitro.

14. The compound according to claim 1, or a stereoisomer, tautomer, prodrug, or pharmaceutically acceptable salt thereof, wherein $R^1$ is fluorine or bromine, and $R^2$ is halogen.

15. The compound according to claim 1, or a stereoisomer, tautomer, prodrug, or pharmaceutically acceptable salt thereof, wherein the alkyl is methyl, ethyl or propyl.

* * * * *